United States Patent [19]
Froix et al.

[11] Patent Number: 5,256,400
[45] Date of Patent: Oct. 26, 1993

[54] PRESSURIZED PRODUCT DELIVERY SYSTEMS

[75] Inventors: Michael Froix, Mountain View, Calif.; Larry Shipley, Lafayette, La.; Christine J. Y. Liau, La Palma, Calif.; Hien Nguyen, Los Osos, Calif.; Sok L. Khor, Palo Alto, Calif.

[73] Assignee: Advanced Polymer Systems, Inc., Redwood City, Calif.

[21] Appl. No.: 803,298

[22] Filed: Dec. 4, 1991

[51] Int. Cl.$^5$ .............................................. A61L 9/04
[52] U.S. Cl. ...................................... 424/45; 424/487; 424/489; 424/501
[58] Field of Search ................... 424/45, 501, 487, 489

[56] References Cited

U.S. PATENT DOCUMENTS

| | | | |
|---|---|---|---|
| 4,690,825 | 9/1987 | Won | 424/501 |
| 4,806,360 | 2/1989 | Leong et al. | 424/487 |
| 4,855,144 | 8/1989 | Leong et al. | 424/487 |
| 4,873,091 | 10/1989 | Jankower | 424/489 |

FOREIGN PATENT DOCUMENTS 0385773  1/1990  European Pat. Off.
001244  4/1983  PCT Int'l Appl.

Primary Examiner—Thurman K. Page
Assistant Examiner—William E. Benston, Jr.
Attorney, Agent, or Firm—Townsend and Townsend Khourie and Crew

[57] ABSTRACT

An apparatus for dispensing pressurized material is comprised of a container, a polymeric matrix having a network of macropores located within the container, and a propellant that may be reversibly sorbed with the network of macropores so as to desorb as the partial pressure of the propellant within the container decreases. The network of pores is substantially non-swellable upon sorption and desorption of the propellant during filling and use of the dispensing apparatus. The polymeric matrix may comprise aggregates of macroporous polymeric particles in which the particles define a substantially non-collapsible pore network and the aggregates define interstitial spaces between the particles, and the interstitial spaces are substantially larger than the pore network.

7 Claims, 3 Drawing Sheets

PRESSURIZED PRODUCT DELIVERY SYSTEMS

BACKGROUND OF THE INVENTION

The present invention relates generally to systems for storing and dispensing gases, liquids, and/or solids. More particularly, the present invention relates to pressurized delivery systems and materials and methods for producing such systems.

Pressurized systems are widely used for dispensing a variety of consumer and industrial products including shaving cream, non-stick cooking products, hair spray, insect repellant, spray paint, and a wide variety of cleaning materials. These systems, which are usually referred to as "aerosols," commonly include three components: (1) a product to be dispensed, (2) a propellant, and (3) a pressurized container including a valve actuator (commonly a push button). The container is typically cylindrical, usually being fabricated as a sheet metal can capable of withstanding moderate pressures. In operation, a push button or other actuator opens the valve which will allow the product to be expelled from an opening or nozzle as a wet spray, fine spray, powder, foam or paste depending upon the application. The propellant, which is typically a gas under ambient conditions, is in most cases expelled from the container with the dispensed product.

The propellant and dispensed product combination may take the form of a solution, emulsion or powder within the aerosol container. In a solution, the propellant is at least partially miscible in the product. In an emulsion, the propellant forms an internal phase which vaporizes on discharge. Shaving cream is a product commonly sold with an emulsion-based dispenser system. Powder systems require a dispersion of the product in the propellant and must be specially designed to avoid clogging of the valve or nozzle during discharge.

As the above examples suggest, in most applications the propellant gas is intimately mixed with the product. In some systems, however, the propellant gas is separated from the product by a mechanical barrier such as a piston or diaphragm which prevents the propellant from passing into the product. These systems are described in European Patent Specification EP0089971 which is incorporated herein for all purposes.

A number of practical considerations limit the substances which can be used as propellant gases and/or the circumstances in which a given substance can be used as a propellant gas. Traditionally, these have included the ability to sustain pressure within acceptable limits during use, safety factors such as the flammability and toxicity of the propellant, and chemical reactivity of the propellant with the container and, mainly in the case of non-barrier dispensers, reactivity of the propellant with the product to be dispensed. For some applications, the flammability provides a particular problem. For example, many non-stick vegetable oil products will be used near an open gas flame or hot stove. Today, the environmental impact of the propellant must also be considered.

The principal advantage of liquefied propellant is their ability to provide a constant pressure within the aerosol container throughout the life of the product. Chlorofluorocarbons ("CFC"s) and low molecular weight hydrocarbons such as propane, butane and isobutane are the most common liquefied propellants. Because these compounds are liquid at the moderate pressures of aerosol containers, the internal pressure of the container is determined by the propellant's vapor pressure. As long as the propellant is present in liquid form within the container (typically the entire life of the product), the pressure will remain nearly constant and the product will be dispensed in the same condition. Consumers today expect this performance from aerosol containers.

Unfortunately, the liquid propellants in widespread use are either environmentally destructive or flammable and toxic. Evidence is mounting that CFCs are destroying the protective ozone layer high in the atmosphere, thus permitting dangerous levels of ultra-violet radiation to reach the earth surface. In response, the countries of the world have taken steps to curtail the use of CFCs and other commonly used propellants. Thus alternative dispensing systems will need to be developed.

One alternative to freon and hydrocarbon propellants is compressed "safe" gas propellants such as nitrous oxide, nitrogen, and carbon dioxide. Unlike the liquid propellants, these gases are nontoxic, low in cost and quite inert. Unfortunately, they can not be liquefied at moderate pressures. Thus, the internal pressure of "safe" gas aerosol containers quickly decreases as the gas—and hence the product—are discharged. The rate at which the product is dispensed and the consistency (whether it be foam, aerosol spray, or liquid) will thus vary over the life of the product. Hence these products are unacceptable for most consumer uses.

As a partial solution to this pressure decay problem, liquid solvents capable of dissolving the safe gas have been included within the dispenser. In theory, the dissolved gas should come out of solution as the vapor phase gas is discharged, thus maintaining an even pressure throughout the product's life. Ethanol may, for example, be used as a solvent when cosmetic products are to be dispensed, and acetone or petroleum distillates may be used when insecticides or paints are to be dispensed. However, these applications are generally limited because the propellant is often relatively insoluble or otherwise incompatible in dispensed product.

Another attempt to employ safe gas propellants in a pressurized dispensing apparatus is described in European Patent Application 385 773 which is incorporated herein by reference for all purposes. According to that application, carbon dioxide or other gaseous propellant is stored—alone or with a liquid solvent—in a "swellable" polymeric material contained within an aerosol dispenser. The propellant is held in microvoids located between the individual molecules of the polymeric material. Thus, the polymeric material acts as a reservoir for the propellant gas, allowing greater amounts of gas to be stored within a pressurized container. As the container is discharged and the internal pressure begins to drop, the polymeric material will release the stored gas, mitigating the pressure loss, and, in theory, provide more uniform product properties over the life of the container. Unfortunately, the polymeric materials discussed in EP 385 773 swell as the container is charged, allowing only a limited amount of propellant to be sorbed before the available container space is completely occupied by the polymer/propellant composition. And on discharge, the volume of the polymer decreases resulting in less head space, less available pressure and, less efficient dispensing near the end of the product's useful life.

Accordingly, there exists a need for improved pressurized dispensing apparatus which have enhanced capacity for propellants, particularly "safe" propellants as described above, but which do not suffer from the disadvantages noted above. In particular, the dispensing apparatus should employ a reservoir which does not expand to fill a major portion of the dispenser volume, and the dispenser should not exhibit substantial pressure decay during the life of the product.

SUMMARY OF THE INVENTION

The present invention provides improved pressurized dispensing apparatus, compositions, and methods for using the apparatus. The apparatus will employ a "reservoir" of gas propellant reversibly sorbed within a substantially non-collapsible pore network defined by a matrix of rigid macroporous polymeric particles within a container. By maintaining such a reservoir, the propellant will be released within the container as the partial pressure is depleted through use. Thus, the present invention is able to employ a wide variety of propellants including those which are not liquids at room temperature and moderate pressure, and particularly including safe propellants as described above.

The non-collapsible particle porous matrix of the present invention has significant advantages over the swellable matrices described above. In particular, the matrices of the present invention will not expand to fill the container as the propellant is added to the apparatus and will not shrink to increase the headspace in the container during normal use, i.e. discharge. Thus, a higher pressure can be maintained over the course of the product's life. In addition, some swellable polymers are made from particularly hazardous materials. For example, polyurethane cross linking is employed in some swellable hydrogels (see EP 385 773) which will give off hydrogen cyanide gas when burned.

One aspect of the present invention relates to compositions of matter for storing a propellant under pressure, particularly within a dispensing container. These compositions comprise substantially rigid, crosslinked, polymeric particles that contain a network of macropores. The propellant and, in many cases, a solvent capable of dissolving the propellant are stored within the network of macropores in a manner such that the propellant is reversibly sorbed (i.e. readily desorbed when the pressure decreases). Preferably the polymeric material will be a copolymer of ethylenic monomers. A particularly preferred example is a copolymer of methyl methacrylate and ethylene glycol dimethacrylate. Further, the polymeric particles will preferably have a porosity of at least 30%. Particles with higher porosities are preferred because they have a greater void volume and surface area per unit volume, and hence a greater capacity for storing propellant. In many applications, a solvent may be added to the system to further increase the propellant storing capacity. Preferred solvents will dissolve substantial amounts of propellant. When a solvent of this type is employed, the rigid polymeric materials should be able to take up at least 100% of their own weight in solvent.

Another aspect of the present invention is a pressurized dispensing apparatus comprising a container with a valve, a matrix of substantially rigid macroporous polymeric particles defining a substantially non-collapsible pore network contained within the container, and a propellant reversibly sorbed within the pore network, whereby the propellant pressurizes said container. The rigid polymeric particles and/or pellets of this invention may be combined, together with a propellant and a product, within a container to form a pressurized dispenser. Typically, the dispenser valve can be controlled by a pushbutton or other actuator commonly found on commercial aerosol containers. When the valve is opened by a user, some of the product—which may be any of a variety of consumer and industrial materials—will be expelled from the container, driven by the propellant pressure. The propellant will in some cases be expelled with the product, but in preferred embodiments it will remain confined within the container, as by a piston or flexible diaphragm. The container pressure should not drop below about 15% of its initial value throughout the course of the product's life, and, preferably, will not drop below about 20% of its initial value. Most preferably, the pressure will not drop below 25% of its initial value. Further, the pressure should not decrease to less than about 90%, and preferably not less than about 80%, of its initial value until more than 50% of its total propellant has been expelled.

A preferred rigid macroporous polymeric matrix for storing propellant under pressure is in the form of aggregates of macroporous polymeric particles (sometimes taking the form of hard pellets or tablets). Preferably, the pellets will be between about 5 mm and about 25 mm in diameter and weigh between about 0.1 and about 2 grams. The particles will define a substantially non-collapsible pore network (as described above) with the aggregate further defining interstitial spaces between the particles such that the interstitial spaces are substantially larger than the pore network. Thus, the interstitial spaces will not substantially limit the rate of propellant sorption and desorption from the macroporous network. Further, the pellets will preferably have a hardness of at least 4 kgs as measured by a Penwalt Stokes tablet hardness tester to resist crumbling during transportation or manufacture of the dispenser. In some cases, the aggregates may be at least be partially held together by a binder.

A preferred process for preparing a pellet aggregate for use in pressurized dispensing containers, includes the following steps: (1) mixing substantially rigid crosslinked polymer macroporous particles with a binder to form a mixture of polymer and binder; and (2) compressing the mixture to form a pellet, wherein said particles define a substantially non-collapsible pore network and the pellet defines interstitial spaces between the particles such that the interstitial spaces are substantially larger than the pore network.

Another aspect of the present invention is a method for filling a dispenser with a pressurized material. The method includes the following steps: (1) introducing to a container a matrix of rigid macroporous polymeric particles; (2) introducing to the container a propellant that may be reversibly sorbed within the macroporous polymeric particles; and (3) introducing to the container a product to be dispensed.

Another aspect of the present invention is a method for dispensing a pressurized material from a container having a valve. The process involves opening the valve to permit the pressurized material to exit the container, wherein the container contains a matrix of rigid macroporous polymeric particles having a network of macropores with a propellant reversibly sorbed within the network of macropores. The polymeric particles will preferably have a porosity and a rigidity such that the pressure within the container will not decrease by more than about 80% until 50% of the propellant has been dispensed from the container.

The present invention employs a simple and inexpensive method for making a variety of gas propellants available for use in pressurized dispensing systems. Other features and advantages of the invention will appear from the following description in which the preferred embodiment is set forth in detail in conjunction with the accompanying drawings.

DESCRIPTION OF THE PREFERRED EMBODIMENT

General

Figure 1:
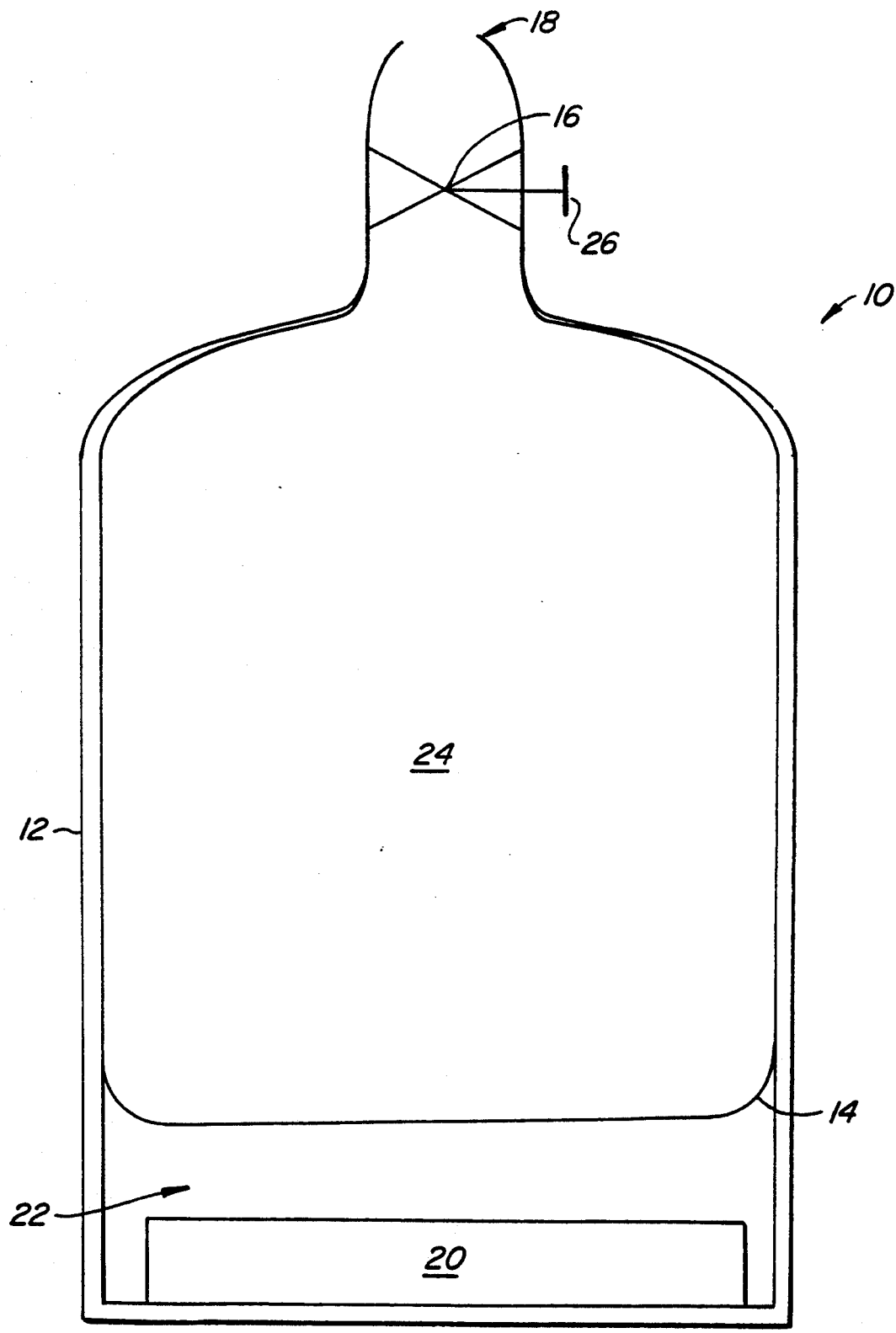
FIG. 1 shows a preferred dispensing apparatus according to the present invention.

The present invention relates to compositions and associated apparatus and methods for storing and releasing a gas or propellant under controlled conditions. This invention employs certain aspects of new aerosol container technologies and macroporous polymeric particle technologies to provide a dispensing system having relatively constant discharge characteristics. In preferred embodiments, a non-toxic, environmentally safe gas can serve as a propellant in an aerosol dispenser used to dispense various consumer and industrial products.

Dispensers of the present invention employ propellant reservoir matrices comprising substantially rigid, crosslinked polymeric particles which are preferably formed as beads. The matrices will provide a macroporous network with pore diameters on the order of micrometers. The polymeric particles of this invention will preferably have a high porosity and substantial rigidity. These and other properties can be controlled by the polymer formation reaction conditions as described in detail below.

The propellant is maintained within the macropores in an amount that will depend upon the partial pressure of the surrounding gas. As the partial pressure of the gas decreases (as is typical during discharge of a gas propellant from an aerosol dispenser), more gas will be freed from the porous network to minimize the loss of partial pressure within the container. Because the polymeric matrix provides a high surface area reservoir for the propellant, more gas can be stored in the pressurized container and more product can be dispensed. And because the polymeric matrices of the present invention are rigid, they will not use up additional space as propellant gas is added to the system. Conversely, as the system is discharged during dispensing, the polymer matrix will not shrink to create more head space. Thus, the macroporous polymeric matrices of the present invention will be better able to maintain high pressures during use of the dispensing apparatus.

In some embodiments of this invention, the polymeric material will be used in conjunction with a solvent for the propellant. Typically, the solvent will permit greater quantities of the gas to stored for use in dispenser. Preferred polymeric particles will be able to absorb at least their own weight in solvent. Some polymeric particles of this invention will typically be able to absorb 1000% and often as much as 1500% or more of their own weight in solvents.

The polymeric particles of this invention are preferably aggregated or "pelletized" to facilitate handling during the manufacturing process. Particles of light, non-aggregated powders are more difficult to add to the container than heavier pellets during assembly of the dispensing apparatus. Relatively fewer pellets need to be added to a container. In addition, expensive filtration systems for removing dust from the air may be necessary in manufacturing facilities where light powdery particles are employed. Such filtration systems are not necessary when pellets are used in manufacturing. The pellets formed according to the present invention are preferably sufficiently hard and crumble resistent to withstand transportation and manufacturing procedures. They may be formed by standard wet or dry granulation techniques employing standard pelletizing machinery. In general, pelletized polymeric particles are preferred because they are more economical to use in the dispenser manufacturing process.

Relative to the unpelletized macroporous polymeric particles, pellets will often have a slightly reduced capacity for the propellant and solvent because of the presence of some binder. In addition, the propellant must be transported by diffusion or some other process to and from the interior of the pellet. This effect, however, is minor because pellets are so that the interstitial spaces between the individual particles are substantially larger than the macropores (where the propellant is stored) within the individual polymer particles. Further, pelletized polymers still have enough propellant capacity to perform satisfactorily. Thus, any disadvantage associated with pelletizing is more than offset by the manufacturing advantage.

Definitions

Certain terms used herein are intended to have the following general definitions:

"Reversibly sorbed" refers to a material such as a propellant gas or a solvent that is absorbed or adsorbed or otherwise taken up by another material, typically a solid or liquid, such that the sorbed material is taken up as its partial pressure increases and released as its partial pressure decreases.

"Substantially rigid" refers to a material such as a macroporous polymer particle that will not change volume by more than 10% during a given process such as absorbing a propellant or solvent. Preferably, the material will not swell by more than 5% in volume, and most preferably not more than 1% during a process. For a powdered or granular material, the volume change will be determined with respect to individual particles rather than a collection or agglomeration of such particles.

"Macropore" describes a pore having an average diameter of between about 0.001 and 1 micrometers. These are only average diameters, and a given sample may have a much wider distribution of pore sizes. For example, some pores found in the polymers of the present invention may be as small as 0.0001 micrometers and some may be as large as 3 micrometers. The average values for the diameter account for various pore geometries, as most macropores are not truly cylindrical. Macropores will have a wide range of shapes, lengths and tortuosities that deviate to varying extent from an ideal cylinder. A macropore should be distinguished from a microvoid which refers to the interstices between individual or small groups of molecules. In most instances, substantially less material such as a solvent or propellant can be stored in an individual microvoid than in a macropore.

The Dispensing Apparatus

FIG. 1 shows a preferred dispensing apparatus of the present invention. The dispensing apparatus 10 includes a rigid, pressure-resistant container 12 having a flexible bag or diaphragm 14 (which alternately may be in the form of a piston) disposed within the container interior. The bag 14 contains a product 24 which is to be dispensed from the container through the container nozzle 18. Below the nozzle is a valve 16 which controls the flow of product 24 from container 12 through nozzle 18. The valve is opened and closed by a valve actuator 26 which is activated from the outside of container 12. A rigid macroporous polymeric matrix 2 together with a sorbed propellant (not shown, typically a gas stored within the polymeric matrix) are contained within a propellant chamber 22, the upper surface of which is defined by bag 14. Thus, polymeric matrix 20 is separated from and never directly contacts the product to be dispensed 24. The bag may be permeable to the propellant, in which case the product and propellant will contact one another and the propellant will be expelled from container 12 with the product.

A variety of container shapes, sizes, and construction materials may be employed with the present invention, but preferred containers will be able to withstand pressures of up to about 200 pounds per square inch of pressure, with most preferred containers withstanding pressures of up to about 300 pounds per square inch. The valve actuator may be a pushbutton, a dial, a lever, a sliding button, or any other means suitable for manual operation. The nozzle will typically form the top of the container, but may be located in other positions of the container such as the side. The nozzle may be replaced by other suitable forms of product conduit such as a pipe.

To operate the dispensing apparatus 10, the valve 16 is opened by valve actuator 26 permitting unrestricted flow of the product out of the container 12 through nozzle 18. The propellant pressurizes the container such that the pressure inside the container is higher than the pressure outside the container. Because, the propellant is at least partially blocked by bag 14 from leaving the container, the propellant will exert pressure on the side of bag 14 opposite product 24. Thus, when valve 16 is opened the propellant will press the product out of bag 14 past valve 16 and out nozzle 18. As the product 24 is dispensed, the propellant will either leave with the product, fill the space previously occupied by bag 14 and the product, or do both. The macroporous polymeric matrix 20 contains a network of pores that serve as a reservoir for the propellant (and sometimes a solvent for the propellant). Because the propellant is reversibly sorbed within the network of pores, it will be desorbed as the partial pressure of the propellant decreases within the container interior. Thus, the pressure in container 12 will not decrease as rapidly as if there were no reservoir for the propellant. Preferably, the polymeric particles will have a porosity and a rigidity such that the pressure within the container will not decrease by more than about 80% until 50% of the pressurized product has been dispensed from the container.

The dispenser of FIG. 1 is a "barrier-type" dispenser with a flexible bag surrounding the product. Another type of barrier-type dispenser includes a sliding piston between the product and the propellant. Such dispenser includes mostly the same components as the bag-type dispenser, except that the bag is replaced by a piston. Thus, the propellant exerts force on a piston rather than a bag, and during discharge, the piston is moved toward the nozzle. The piston will form a substantially leak-tight seal with the container wall to separate the propellant from the product to be dispensed. Thus, in a manner similar to the flexible bag of the barrier-type dispenser shown in FIG. 1, the piston of this embodiment maintains the dispensable product out of direct contact with the macroporous polymeric matrix while transmitting the pressure of the propellant gas to the dispensable product for controlled release through the valve. The piston-type dispenser does not release propellant gas into the atmosphere in normal operation.

In other embodiments, the product will not be separated from the propellant and polymeric matrix by a bag, piston, diaphragm or other means. In these embodiments, the propellant, product, and polymeric matrix will be present in a common chamber, and the propellant will be dispensed along with the product. These systems will typically contain many components in common with the bag-type dispenser described above. Such barrier-free embodiments may further comprise a screen, filter, or the like, to prevent plugging of the valve and nozzle by the polymeric particles or aggregates.

During manufacture, the propellant, macroporous polymeric matrix and solvent, if any, must be added to the dispenser container. It is important that the correct amount of propellant is placed in the container before the propellant chamber is sealed. Too little propellant will result in insufficient internal pressure to effectively dispense the product, whereas too much propellant will result in excess internal pressure with a consequent danger of the dispenser bursting. If the propellant is carbon dioxide or other gas that can easily be condensed, the amount of propellant to be added to the container can be determined by simply providing the propellant in the form of a liquid or relatively uniform pellets of frozen material (e.g. dry ice). As for the solvent, it can be easily metered by simple volumetric measurement, or by direct weighing.

However, since the solid or liquid propellants will likely have a very low temperature (around −80 degrees Centigrade for dry ice), their simple addition to the solvent at ambient temperature will lead to rapid vaporization of the propellant, and consequent loss of propellant gas instead of its necessary sorption in the solvent. One way to mitigate this loss is by first chilling the solvent (acetone may be used with dry ice) to near the temperature of the condensed or sublimed propellant. For example, the solvent can be first chilled to approximately the temperature of the liquefied or solidified propellant. This procedure is described in more detail together with three other procedures in EP 385 773. These procedures will be briefly discussed below.

The first procedure is employed with a dispenser of the type described in European Patent Specification EP 0089 971. In this procedure, the propellant chamber is accessible at the lower end of the dispenser by a filing hole sealable by a plug. The requisite quantity of gas-free liquid solvent is poured through the filling hole into the propellant chamber while the dispenser is inverted. Then the appropriate quantity of liquefied or pelletized propellant (e.g. 1 or more pellets of carbon dioxide) together with the polymeric matrix (preferably pelletized) is added through the filling hole and the plug is immediately inserted to seal the propellant chamber. If the plug is immediately applied, relatively little propellant gas will be lost by vaporization and venting. The sealed dispenser may then be agitated to assist sorption of the rapidly vaporizing propellant in the solvent. The risk of this procedure lies in a probable over-pressurization of the dispenser in the interval between vaporization and sorption of the propellant with a consequent risk of the dispenser bursting. Further, control of resultant propellant pressure may be difficult because of the time-critical nature of the procedure.

The second procedure is a modification of the first procedure in that the pellet(s) of carbon dioxide (or other solidified propellant) are wrapped in a small piece of paper or other suitable material of relatively low thermal conductivity prior to being dropped through the filling hole into the propellant chamber. The wrapping material may be soluble or insoluble in the acetone or other liquid solvent(s) employed. The paper acts as a thermal barrier which delays vaporization of the frozen propellant by contact with the relatively hot (ambient temperature) solvent, allowing more time in which to add the macroporous polymeric particles or pellets and insert the plug into the filling hole before significant loss of propellant gas occurs. The small piece of paper remains in the sealed propellant chamber but does not significantly or adversely affect the normal operation of the dispenser.

In the third procedure (described above), the carbon dioxide or other propellant is added to the solvent while the solvent is outside the pressurized dispenser. Premature vaporization of the propellant is obviated by pre-chilling the solvent to approximately the temperature of the subsequently added propellant. The macroporous polymeric particles or pellets are added contemporaneously with the solvent and propellant. According to EP 385 773, a batch process was employed in which approximately 10 milliliters of liquid acetone was chilled to a temperature of about −80 degrees Centigrade (comfortably above the freezing point of commercial-purity acetone). A carbon dioxide pellet with a nominal weight of 1.5 grams was then added to the pre-chilled acetone. The thermal interaction of the acetone with the carbon dioxide was minimal since both substances had approximately equal temperatures. Moreover, the adsorption of a small quantity of carbon dioxide into acetone at a temperature of −80 degrees Centigrade would take place instantly. The resultant carbon dioxide/acetone composite was then transferred into the propellant chamber of the dispenser container before significant warming took place, and the propellant chamber was promptly sealed. When the temperature of the dispenser stabilized at ambient indoor temperature ("room temperature"), the dispenser was fully pressurized within acceptable tolerances for initial pressurization, and ready for use.

The fourth procedure is similar to the third procedure in that the acetone or other solvent is pre-chilled to a predetermined temperature, but differs in that the carbon dioxide or other propellant is added as a gas to the pre-chilled solvent. Thus, the gas is pre-dissolved in the solvent, and only the solvent and polymeric material need be added to the dispenser container. According to EP 385 773, −55 degrees Centigrade has been established to be the exact temperature at which the acetone should be maintained while gaseous carbon dioxide is bubbled through the acetone. This will permit the acetone to absorb the correct proportion of carbon dioxide for subsequent use as a propellant in a standard piston-barrier pressurized dispenser as manufactured and sold by Rocep-Lusol Limited of Great Britain. Absorption of carbon dioxide in acetone at that temperature is quickly achieved. The liquid mixture of carbon dioxide and acetone at −55 degree Centigrade is then transferred directly into the dispenser container. Only when the temperature increases from −55 degrees Centigrade does carbon dioxide start to boil off. This temperature control is therefore a way of accurately metering the volume of carbon dioxide required for a given volume of acetone.

Polymeric Material

Polymeric particles useful in the present invention each define a network of internal pores open to the exterior of the particle, which pores are capable of reversibly sorbing a propellant and optionally other fluid of interest. The particles will be substantially rigid so that the pore network is non-collapsible, preferably being formed from highly crosslinked copolymers as described in detail below. In particular, the polymeric particles will be non-swellable in the propellant and solvent used in the delivery system, thus avoiding the problems with swellable matrices described above.

The rigid polymer particles of the present invention will have greater than 5% cross-linking, usually having in the range from about 10% to 100% cross-linking, more usually having in the range from about 20% to 95% cross-linking, and typically being in the range from about 25% to about 90% cross-linking. The calculated or theoretical percentage of cross-linking is defined as the weight of unsaturated monomer (or monomers) containing more than one unsaturated group divided by the total weight of monomer, including both mono- and poly-unsaturated monomers.

Polymeric particles suitable for use in the present invention will usually be non-toxic. Most particle preparation processes will result in the formulation of spherical beads, but beads having non-spherical asymmetric, and/or irregular geometries will also find use so long as they meet the necessary physical parameters set forth below. Suitable polymeric particles will not readily undergo unwanted reactions, will be stable over a wide pH range, and will resist moderate oxidation and reduction. The particles should be stable at lower as well as higher temperatures and have a relatively long shelf life. Desirable physical parameters for the polymeric particles are as follows:

|  | Broad Range | Preferred Range |
| --- | --- | --- |
| Particle Size | 1–500 $\mu$m | 2–150 $\mu$m |
| Particle Density | 0.1–2.0 g/cc | 0.2–1.5 g/cc |
| Pore Volume | 0.5–6.0 cc/g | 1.0–5.0 cc/g |
| Avg. Pore Diameter | 0.001–3 $\mu$m | 0.003–1 $\mu$m |

|              | Broad Range | Preferred Range |
|--------------|-------------|-----------------|
| Surface Area | 1–500 m²/g  | 20–200 m²/g     |

Following conventional methods of measuring and expressing pore sizes, the pore diameters are measured by techniques such as nitrogen or mercury porosimetry and are based on the model of a pore having a cylindrical shape.

The particles may be formed from a wide variety of polymers, including polyvinyl alcohol, polyethylene, polypropylene, polystyrene, polyacrylamide, polyether, epoxy, ethylene vinyl acetate copolymer, polyvinylidene chloride, polyvinyl chloride, polyacrylate, polyacrylonitrile, chlorinated polyethylene, acetal copolymer, polyvinyl pyrrolidone, poly(p-xylene), polymethylmethacrylate, polyvinyl acetate, and polyhydroxyethyl methacrylate. Preferably the polymers will have some degree of crosslinking. Thus, the above polymers will only rarely be employed in pure form. More commonly, copolymers will be formed that include monomers used to produce the above polymers.

Thus, at least one monomer should be polyethylenically unsaturated, and usually the polymer will include a monoethylenically unsaturated co-monomer. The degree of cross-linking may then be controlled by adjusting the ratio of monoethylenically unsaturated monomer to polyethylenically unsaturated monomer, as discussed in more detail hereinbelow.

Monoethylenically unsaturated monomers suitable for preparing polymer particles for the polymer delivery system include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sebutyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate, vinyl stearate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isoprene, butadiene and chloroprene, may be used as part of the monoethylenically unsaturated monomer content.

Polyethylenically unsaturated cross-linking monomers suitable for preparing such polymer particles include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithioderivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The particularly preferred polymer system of the present invention is formed by the copolymerization of methylmethacrylate and ethylene glycol dimethylmethacrylate. Usually, the methylmethacrylate will be present at from about 10 to 80 percent of the monomer mixture, more usually at about 20 to 70 percent of the monomer mixture, typically being in the range from about 25 to 65 percent of the monomer mixture, with the ethylene glycol dimethylmethacrylate forming the remainder of the mixture.

The preferred polymer particle matrix of the present invention comprises rigid polymeric particles having a substantially non-collapsible pore structure. That is, the particles will substantially retain their internal pore structure even after the porogen (used in formation of the particle as described hereinafter) has been extracted and the pores are empty. Such particles are mechanically stable compared with non-rigid materials, allowing manufacturing, processing, and handling of the particles under relatively rigorous conditions which might result in the rupture or damage of less stable materials. More importantly, the non-collapsible pores facilitate formation of hard pellets or tablets and introduction of the propellant or propellant solvent as described in more detail hereinafter.

A polymeric particle of the present invention can be prepared by polymerizing one or more polymers by a free radical suspension polymerization process. A monomer or pair of comonomers is dissolved in an inert porogen, which is also the active ingredient, to form a solution which is suspended in a phase or solvent incompatible with the solution.

An example of a phase or solvent might be water with stabilizing additives. After the solution is suspended in the phase, the solution and phase are agitated to form a plurality of droplets of solution suspended in the phase. After the formation of the plurality of droplets are activated to initiate a polymerization reaction in which a monomer is cross-linked or two or more monomers are polymerized to form porous particles having a network of pores with the porogen held within the network of pores. The activation may be triggered by an initiator which is soluble in the monomer solution. Alternatively, activation may be triggered by an energy source such as radiation. The inert porogen will serve as an internal diluent during polymerization to introduce the desired sponge-like macroporous structure or network of pores into the finished particle. The inert porogen should not react with the monomer present during polymerization or inhibit the polymerization. After the formation of the porous particles, the particles are separated from the phase and may be subjected to one or more purification steps, such as washing, to remove any unreacted monomer or impurity from the particles. Typically, the porogen is extracted and the propellant or other additives are introduced by absorption. In some cases, however, it may be desirable to keep the porogen in the particles for use in the aerosol dispenser. For example, the porogen may be a solvent for the propellant.

The process of the present invention can be designed so as to control porosity and the particle diameter of the particles. Under identical polymerization conditions, the porosity can be increased by increasing the calculated or theoretical cross-linking density or by increasing the porogen concentration in the solution. An increase in porosity will increase the surface area of the particle and hence the weight percent of the propellant or solvent that can be held within the particle. Particles having a porosity of greater than 30% are preferred and most preferably the porosity will be greater than 50%. In systems employing a solvent, the polymeric particle should be able to take up at least 100% and in some cases as much as 1500% of its own weight in solvent. To decrease the particle diameter under identical polymerization conditions, the agitation or the concentration of dispersion agents in the phase should be increased. By controlling the particle diameter and particularly the porosity of the particle, a material suitable for use in the method of the present invention can be obtained. Materials suitable as porogens will be liquid substances which meet the following criteria:

1. They are either fully miscible with the monomer mixture or capable of being made fully miscible by the addition of a minor amount of non-water-miscible solvent;
2. They are immiscible with water, or at most only slightly soluble;
3. They are inert with respect to the monomers, and stable when in contact with any polymerization catalyst used and when subjected to any conditions needed to induce polymerization (such as temperature and radiation); and
4. They are readily extracted from the pore network of the particles once polymerization is complete.

Suitable porogens include a wide range of substances, notably inert, non-polar organic solvents. Some of the most convenient examples are alkanes, cycloalkanes, and aromatics. Specific examples of such solvents are alkanes of from 5 to 14 carbon atoms, straight or branched chain cycloalkanes of from 5 to 8 carbon atoms, benzene, and alkyl-substituted benzenes, such as toluene and the xylenes. For purposes of making particles having the high porosity necessary to be used with pressurized propellant systems, it has been found that cyclohexanol and particularly cyclohexanol combined with toluene or dodecanol are preferred porogens.

Extraction of the porogen may be effected by solvent extraction, evaporation, or similar conventional operations. The porogen extraction step accomplishes the removal of unwanted species from the polymerized structures prior to impregnation with the desired active substance. Such unwanted species include unreacted monomers, residual catalysts, and surface active agents and/or dispersants remaining on the particle surfaces.

Extraction of the porogen may be effected in a variety of ways, depending on the chemical nature of the porogen and its behavior in combination with that of the other species present. For example, the particles may be recovered from the suspension by filtration, preferably using vacuum apparatus (such as a Beuchner funnel). The particles are then washed with an appropriate solvent to remove organic species not bound to the polymer, including surfactants having deposited on the particle surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the particles. This again may be followed by drying under vacuum.

Once the particles are rendered dry and free of the porogen and any unwanted organic materials, they may be pelletized and the propellant and, if desired, a solvent for the propellant are introduced to the internal pore networks of the individual particles by absorption, typically in a suitable solvent. Such methods of introducing the propellant will be described in more detail hereinbelow.

Pelletizing the Polymer

The polymeric materials of this invention are initially in the form of light particles or beads which may be employed directly (without modification) in the dispensing systems of the present invention. Unfortunately, small light materials such as these are difficult to add to containers during the manufacturing process (discussed above). Thus, to facilitate manufacturing of pressurized containers, the polymeric particles of this invention may be converted to heavier, rugged pellets before being added to the containers. Delivering the polymer to the aerosol container in tablet form avoids the need for specialized systems necessary for coping with the air-borne particulate and solvents associated with polymer powders or solutions. Thus, significant advantages in the cost and convenience of the manufacturing process can be realized.

The pellets formed according to this invention will have a hardness of greater than about 1 Kilogram as measured by a Penwalt Stokes tablet hardness tester (Penwalt Stokes, Inc., Warminster, Pa.) and will resist crushing, crumbling and fracture. Preferably, the pellets will be harder than about 3 Kgs, and most preferably harder than about 4 Kgs. Thus, they can be safely transported and stored without break-up.

Pelleting or "tableting" can be achieved with or without a binder. A binder may be used to facilitate agglomerating individual particles together to form a pellet. The binder will desirably also provide additional hardness and crumble resistance to the pellet or tablet. Suitable binders include polyvinylpyrrolidone (PVP), polyvinyl alcohol (PVA), polyacrylic acid (PAA), hydrogenated cotton seed oil, hydroxymethyl cellulose, hydroxypropyl cellulose, methylcellulose, carboxymethyl cellulose, microcrystalline cellulose (such as Avicel), lignin sulfate, and other binders commonly used tableting and briquetting operations. Magnesium stearate may also be added to the polymeric material for the purpose of lubricating the material to prevent the pellets from sticking to the die surface.

The polymer particles to be pelletized are preferably pretreated to texturize them or render them "stickier", qualities which have been found to aid in agglomeration and pelletizing. One preferred pretreatment involves washing the polymers alternately in hot water and organic solvent, e.g. acetone, as described in the examples below. Alternatively, unwashed polymer particles can be heated to drive off the volatile porogen without removing the suspending agent such as polyvinylpyrrolidone or polyvinyl alcohol, both of which can serve as a binder. Polymer particles pretreated by the above methods often form agglomerates even before pelletizing. These agglomorates may range in size from a few micrometers to 0.1 millimeter or more.

The tableting procedure may be accomplished with a wet or dry granulation process. In a preferred dry pelletizing procedure performed according to this invention, dry polymeric particles are mixed with a binder (and optionally magnesium stearate) to form a mixture having about 50-100% macroporous polymer, greater than 0% binder, and about 0-15% magnesium stearate by weight. Preferably, the mixture will include about 80-100% macroporous polymer, about 0-20% binder, and about 0-5% magnesium stearate. Most preferably, the mixture will include greater than about 90% macroporous polymer, between about 0-10% binder, and between about 0-2% magnesium stearate. The resulting combination may be tumbled on a roll-mill to assist in the mixing. After sufficient mixing, any large clumps of material are broken up and the particles are reduced to a relatively uniform size by passing the mixture through a screen for example. A mesh screen of greater than about 25 mesh will work well. Preferably, the screen will be between about 10 and 21 mesh, with a most preferable screen being between about 14 and 20 mesh. The resulting granular mixture is compressed in a standard tableting machine.

In a wet granulation procedure, the macroporous polymer is mixed with magnesium stearate and either a dry binder or a wet binder solution. If a dry binder was employed, the mixture may be tumbled to achieve good mixing, and water is then added to dampen the resulting mixture. At this point, either type of mixture may be reduced to granules of the proper size. A mesh screen of greater than about 25 mesh will work well. Preferably, the screen will be between about 10 and 21 mesh, with a most preferable screen being between about 14 and 20 mesh. Other means such as extrusion of a thin strand followed by chopping can be employed to obtain granules of the proper size. The wet granules are next heated or otherwise treated to drive off most of the water. Finally, the dried granules are compressed to hard tablets in a standard tableting machine.

Liquid Solvents

Liquid solvents may be used with the apparatus of the present invention to dissolve additional propellant and thus enhance the sorption capacity of the macroporous polymeric matrix. Suitable solvents will generally dissolve for the propellant gas while being substantially insoluble of the polymeric material. Further, the solvent should not cause the substantially rigid macroporous polymer to swell. Acetone is a particularly preferred solvent when carbon dioxide is used as the propellant gas. Carbon dioxide may also be used with alcohol solvents such as ethyl and methyl alcohol. Nitrous oxide will preferably be used with alcohol (ethyl or methyl) or ether solvents. Solvents for other gaseous propellants are well-known in the art. Suitable solvents may also include water, p-cymene, chloroform, benzene, toluene, acrylonitrile, nitrobenzene, o-dichlorobenzene, ethyl benzoate, methyl methacrylate, benzaldehyde, acetaldehyde, methyl benzoate, dimethyl phthalate, furfural, aniline, butyrolactone, cyclohexanone, acetic acid, m-cresol, quinoline, acrylic acid, benzyl alcohol, propylene glycol and formamide.

While not wishing to be bound by theory, it is believed that the extent to which the polymeric material sorbs the liquid solvent (measured as volume or weight of liquid per unit weight of polymeric material) corresponds to the potential gas storage performance of a given combination of polymeric material and liquid solvent. While the use of substantially pure solvents is envisioned, compatible mixtures of two or more liquid solvents may be suitable for use in certain aspects of the invention. Some such mixtures may be more practicable than pure solvents, as (for example) commercial ethanol often contains a substantial percentage of water.

Minor quantities of impurities normally present in commercial-grade or industrial-grade liquid solvents (as distinct from relatively pure laboratory-grade liquid solvents) are acceptable so long as they do not significantly or adversely affect the basic principles of the present invention in any of its aspects.

In addition to the above-mentioned functional requisites of a technically suitable liquid solvent, regard should also be had to safety factors such as toxicity and environmental hazard. For such reasons, "benign" solvents such as water and lower alcohols (e.g. ethanol) are preferred over known biohazards such as chlorinated hydrocarbons and benzene, but in appropriate circumstances such considerations need not prevent adoption of liquid solvents that would be non-preferred in other circumstances (particularly if containment was assured and recycling was reliable). Other factors, such as economy and availability, may also influence a choice of liquid solvent or solvent mixture. cl Propellant Gases A wide variety of conventional propellant gases may be employed in the dispenser systems of the present invention, while environmentally benign gases such as carbon dioxide, nitrous oxide, nitrogen, oxygen, and mixtures of these such as nitrogen/oxygen mixtures including "natural" air are preferred, other conventional propellants may be adopted, for example ammonia or sulphur dioxide. The present invention may even be used with problematic gases, such as freon and hydrocarbons, although such use is not preferred for the reasons stated above. Minor quantities of impurities normally present in commercial-grade or industrial-grade gases (as distinct from relatively pure laboratory-grace gases) may be present in the propellant(s) so long as they do not significantly or adversely affect the basic principles of the present invention in any of its aspects.

The propellant gas may be converted to a cryogenically cool=d liquid or solid such as "dry ice" in the case of carbon dioxide. Where the propellant gas is solidified, the solidified gas is preferably pelletized or in particulate form for greater ease of separating and metering the substantially predetermined amount of propellant gas from a bulk supply thereof. The polymeric material and solvent (when applied) may also be pelletized or in particulate form for greater ease of separating and metering the substantially predetermined quantity thereof into the pressurizable container.

Products to be Dispensed

In general, any substance which is dispensable from a pressurized container is suitable for use with the present invention, subject to such practical limitations as the compatibility of the product with the propellant in non-barrier and semi-permeable barrier systems. Suitable substances for dispensing from a pressure pack dispenser include lubricant compositions, anti-corrosion agents, de-icers, sealing compounds, paints, insecticides, polishes, cosmetics, shaving cream, non-stick cooking products, hair spray, cleaning materials and pharmaceutical substances.

In some instances, the propellant will be dispensed with the product and may even be necessary to impart a particular consistency or form to the product. For example, in some lubricants and hygiene products, the combination of the dispenser and the propellant system functions as a foam generator.

It is also within the scope of the present invention that the propellant gas constitutes part of the dispensed product for example as inflation gas for inflating articles such as tires or balloons, as gaseous fuel or oxidizer in combustion, cutting, or welding systems, as a breathing gas or breathing gas mixture, and as an industrial or laboratory gas.

The invention will be further illustrated in the examples that follow wherein the polymeric material is a copolymer of methyl methacrylate and ethylene glycol dimethacrylate.

Experimental

Example 1: Methyl Methacrylate High Acetone Absorption Polymers, 20% Cross-linking and Use Dodecanol and Cyclohexanol as Porogens 29.03 g of dodecanol and 240.97 g of cyclohexanol were melted in a beaker at 60° C. to form a porogen mixture. Then 0.45 g of AIBN (2,2 azobisisobutyronitrite) and a mixture of 24 g of methyl methacrylate and 6.0 g of ethylene glycol dimethacrylate were dissolved in the porogen mixture. The resulting solution was combined with a mixture of 9.00 g of a 20% aqueous solution of polyvinylpyrrolidone (MW 700,000 PVP K-90 from GAF Chemical Corp. of Wayne, N.J.) and 600 g of deionized water in a vessel provided with a agitator, a thermometer, a nitrogen inlet and reflux condenser. To avoid clumping, the temperature was slowly increased from room temperature to 60° C. over 30 minutes. The exothermic polymerization starts at about 57° C. as indicated by a temperature increase. After one hour, the nitrogen gas supply was disconnected. Polymerization was carried out at about 75° C. for 8 hours at a stirring speed of 730 rpm. When the reaction was completed, the product was filtered with hot water to remove the PVP K-90. Then the polymer washed alternately with hot water and acetone until the filtrate was colorless. The resulting polymers were dried in a vacuum oven at 80° C. for 8 hours.

Example 2: Methyl Methacrylate High Acetone Absorption Polymers, 40% Cross-Linking and Use Dodecanol and Cyclohexanol as Porogens 29.03 g of dodecanol and 240.97 g of cyclohexanol were melted in a beaker at 60° C. to form a porogen mixture. Then 0.45 g of AIBN (2,2 azobisisobutyronitrite) and a mixture of 18 g of methyl methacrylate and 12 g of ethylene glycol dimethacrylate were dissolved in the porogen mixture. The resulting solution was combined with a mixture of 6.75 g of a 20% aqueous solution of polyvinylpyrrolidone (MW 700,000 PVP K-90 from GAF Chemical Corp. of Wayne, N.J.) and 450 g of deionized water in a vessel provided with a agitator, a thermometer, a nitrogen inlet and reflux condenser. To avoid clumping, the temperature was slowly increased from room temperature to 60° C. over 30 minutes. The polymerization starts at about 57° C. After one hour, the nitrogen gas supply was disconnected. Polymerization was carried out at about 75° C. for 8 hours at a stirring speed of 730 rpm. When the reaction was completed, the product was filtered with hot water to remove the PVP K-90. Then the polymer washed alternately with hot water and acetone until the filtrate was colorless. The resulting polymers were dried in a vacuum oven at 80° C. for 8 hours.

Example 3: Methyl Methacrylate High Acetone Absorption Polymers, 40% Cross-Linking and Use Toluene and Cyclohexanol as Porogens 27 g of toluene and 243 g of cyclohexanol were stirred in a beaker until the cyclohexanol was completely dissolved. Then 0.45 g of AIBN (2,2 azobisisobutyronitrite) and a mixture of 18 g of methyl methacrylate and 12 g of ethylene glycol dimethacrylate were added to the toluene-cyclohexanol mixture. The resulting solution was combined with a mixture of 9.00 g of a 20% aqueous solution of polyvinylpyrrolidone (MW 700,000 PVP K-90 from GAF Chemical Corp. of Wayne, N.J.) and 600 g of deionized water in a vessel provided with a agitator, a thermometer, a nitrogen inlet and reflux condenser. To avoid clumping, the temperature was slowly increased from room temperature to 60° C. over 30 minutes. The polymerization starts at about 57° C. After one hour, the nitrogen gas supply was disconnected. Polymerization was carried out at about 75° C. for 8 hours at a stirring speed of 730 rpm. When the reaction was completed, the product was filtered with hot water to remove the PVP K-90. Then the polymer washed alternately with hot water and acetone until the filtrate was colorless. The resulting polymers were dried in a vacuum oven at 80° C. for 8 hours.

Example 4: Methyl Methacrylate High Acetone Absorption Polymers, 70% Cross-Linking and Use Toluene and Cyclohexanol as Porogens 54 g of toluene and 486 g of cyclohexanol were stirred in a beaker until the cyclohexanol was completely dissolved. Then 0.90 g of AIBN (2,2 azobisisobutyronitrite) and a mixture of 18 g of methyl methacrylate and 42 g of ethylene glycol dimethacrylate were added to the toluene-cyclohexanol mixture. The resulting solution was combined with a mixture of 9.00 g of a 20% aqueous solution of polyvinylpyrrolidone (MW 700,000 PVP K-90 from GAF Chemical Corp. of Wayne, N.J.) and 600 g of deionized water in a vessel provided with a agitator, a thermometer, a nitrogen inlet and reflux condenser. To avoid clumping, the temperature was slowly increased from room temperature to 60° C. over 30 minutes. The polymerization starts at about 57° C. After one hour, the nitrogen gas supply was disconnected. Polymerization was carried out at about 75° C. for 8 hours at a stirring speed of 850 rpm. When the reaction was completed, the product was filtered with hot water to remove the PVP K-90. Then the polymer washed alternately with hot water and acetone until the filtrate was colorless. The resulting polymers were dried in a vacuum oven at 80° C. for 8 hours.

Example 5: Methyl Methacrylate High Acetone Absorption Polymers, Replace PVP K-90 with PVOH 29.03 g of dodecanol and 240.97 g of cyclohexanol were melted in a beaker at 60° C. to form a porogen mixture. Then 0.45 g of AIBN (2,2 azobisisobutyronitrite) and a mixture of 24 g of methyl methacrylate and 6.0 g of ethylene glycol dimethacrylate were dissolved in the porogen mixture. The resulting solution was combined with a mixture of 7.5 g of polyvinylalcohol (MW 78,000, 88% hydrolyzed) and 300 g of deionized water in a vessel provided with a agitator, a thermometer, a nitrogen inlet and reflux condenser. To avoid clumping, the temperature was slowly increased from room temperature to 60° C. over 30 minutes. The polymerization starts at about 57° C. After one hour, the nitrogen gas supply was disconnected. Polymerization was carried out at about 75° C. for 8 hours at stirring speed of 730 rpm. When the reaction was completed, the product was filtered with hot water to remove the polyvinylalcohol. Then the polymer washed alternately with hot water and acetone until the filtrate was colorless. The resulting polymers were dried in a vacuum oven at 80° C. for 8 hours.

Example 6: Methyl Methacrylate High Acetone Absorption Polymers, Without Suspending Agent Present in the Aqueous Phase 29.03 g of dodecanol and 240.97 g of cyclohexanol were melted in a beaker at 60° C. to form a porogen mixture. Then 0.45 g of AIBN (2,2 azobisisobutyronitrite) and a mixture of 24 g of methyl methacrylate and 6.0 g of ethylene glycol dimethacrylate were dissolved in the porogen mixture. The resulting solution was mixed 300 g of deionized water in a vessel provided with a agitator, a thermometer, a nitrogen inlet and reflux condenser. To avoid clumping, the temperature was slowly increased from room temperature to 60° C. over 30 minutes. The polymerization starts at about 57° C. After one hour, the nitrogen gas supply was disconnected. Polymerization was carried out at about 75° C. for 8 hours at a stirring speed of 730 rpm. When the reaction was completed, the product was filtered with hot water. Then the polymer washed alternately with hot water and acetone until the filtrate was colorless. The resulting polymers were dried in a vacuum oven at 80° C. for 8 hours.

Example 7: 70% Cross-Linking with Dodecanol and Cyclohexanol as the Porogen 29.03 g of dodecanol and 240.97 g of cyclohexanol were melted in a beaker at 60° C. to form a porogen mixture. Then 0.45 g of AIBN and a mixture of 9 g of methyl methacrylate and 21 g of ethylene glycol dimethacrylate were dissolved in the porogen mixture. The resulting solution was combined with a mixture of 6.75 g of polyvinylpyrrolidone (PVP K-90) and 450 g of deionized water. Polymerization and treatment of the polymer was carried out as described in Example 1.

Example 8: Changing the Porogen to Monomer Ratio from 90/10 to 70/30

7.53 g of dodecanol and 62.47 g of cyclohexanol were melted in a beaker before being dissolved in 0.3 g of AIBN and a mixture of 18 g of methyl methacrylate and 12 g of ethylene glycol dimethacrylate. The resulting solution was then added to 180 g of deionized water containing 2.7 g of 20% aqueous solution of polyvinylpyrrolidone (PVP K-90). The polymerization and treatment of the polymer was carried out as described in Example 1.

Example 9

A mixture of 2017.5 grams of toluene and 1788 grams of cyclohexanol was used as a porogen. 16.8 grams of benzoyl peroxide, 201.7 grams of methyl methacrylate and 470 grams of ethylene glycol dimethacrylate were added to the porogen. The resulting solution was combined with a mixture of 56.3 grams of methylcellulose ("Methocel", Dow Chemical Co., Midland, Mich.) and 5377 grams of deionized water. Polymerization and treatment of the polymer was carried out as described in Example 1.

Example 10: Dry Granulation

Polymer particles produced as described in Example 1 were mixed with an inert binder of hydrogenated cottonseed oil (Tradename Duratex) in a ratio of 9 parts polymer to 1 part Duratex. Magnesium stearate was added to the mixture at a level of 1% of the total weight of the mixture. The mixture was then screened to remove lumps.

Tablets were made on a standard tableting machine (Penwalt Stokes, Inc., Warminster, Pa). The resulting tablets had diameters ranging from 15 mm to 9 mm and weights ranging from 0.3 grams to 0.6 grams.

The tablets produced exhibited hardness ranging from 7.5 kgs to 13 kgs when the hardness was measured by a Penwalt Stokes tablet hardness tester.

The acetone pick-up of the tablets were measured and compared to the untableted polymer containing no binder or magnesium stearate.

|  | Acetone pick-up/gm of polymer or tablet |
|---|---|
| Polymer tablet | 9 gms |
| Untableted Polymer | 10 gms |

Example 11: Dry Granulation

Polymer particles made as described in Example 2 were blended with a microcrystalline cellulose (tradename Avicel) and magnesium stearate in weight ratios of 90 parts polymer 10 parts avicel and 1 part magnesium stearate. The blend was tumbled on a roll-mill to assist mixing of the blend.

0.30 gm tablets were made from the blend. The tablets exhibited a hardness of 9.5 kgs. The acetone pick-up of the untableted polymer and the tablets was as follows:

|  | Acetone pick-up/gm of polymer or tablet |
|---|---|
| Polymer tablet | 10.6 gms |
| Untableted Polymer | 9.7 gms |

Example 12: Wet Granulation

Polymer particles made as described in Example 3 were blended with polyvinyl alcohol (PVOH) and magnesium stearate in the proportions of 90 gms polymer, 10 gms PVOH and 1 gm of magnesium stearate. Enough water was added to the blend to facilitate uniform mixing of the components of the blend and to achieve a damp mixture in which no excess water could be squeezed from the mixture.

The wet mixture was passed through a 20 mesh screen to form granules. The granules were dried in an oven at 70° C. for 8 hours.

The dry granules were tableted to produce 0.35 gm tablets having hardness of 9.5 kgs.

Acetone pick-up after tableting was 8.5 gms per tablet compared to 9.5 gms per gram of untableted polymer.

Example 13: Wet Granulation 100 grams of polymer particles from Example 4 was mixed with 30 grams of powdered polyvinylpyrrolidone and 1 gram of magnesium stearate. The blend was tumbled to achieve good mixing. 100 cc of water was added to the mixture and mixed in. The mixture was passed through a 14 mesh screen. The granules thus formed were dried in an oven at 60° C. for 10 hours. The granules were formed into tablets, each having a weight of 0.5 grams.

Example 14: Wet Granulation 100 grams of polymer particles as produced in Example 5 was mixed with 1 gram magnesium stearate and 300 grams of a 10% solution methyl cellulose (Methocel). The mixture was blended together, passed through a 20 mesh screen and the granules dried in an oven at 70° C. overnight. The dried granules were made into 0.5 gm tablets.

The tablets were evaluated for hardness and its ability to withstand abuse by attempting to crush a tablet between the thumb, index finger and middle finger of one hand, and by allowing the tablet to fall to the floor from a height of 8 feet. The tablets were strong and rugged enough to withstand such abuse.

Discharge Characteristics

Figure 2:
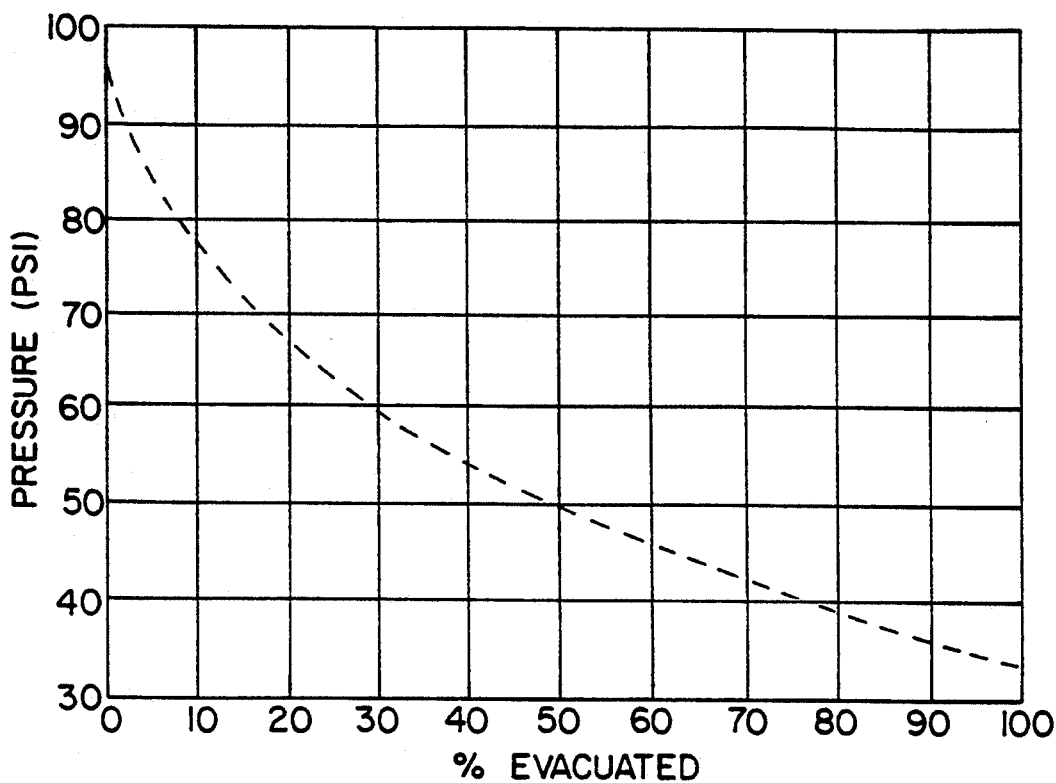
FIG. 2 is a graph of pressure versus depth of discharge for a dispenser employing a carbon dioxide propellant, acetone and a preferred macroporous polymeric matrix according to the present invention.

FIG. 2 shows the discharge curve for a pressurized, vapor-tight container charged with 1.13 g carbon dioxide, 8.4 ml acetone and 1.53 g polymer produced as in Example 2. A bag-type dispenser (as described above) outfitted with a pressure gauge was used to make the measurements. As shown, the pressure is initially near 100 psi and drops off gradually as the container is evacuated until a final pressure of about 38 psi is reached. The polymers employed in this test had a porosity of greater than 3.0 cc/gram.

Figure 3:
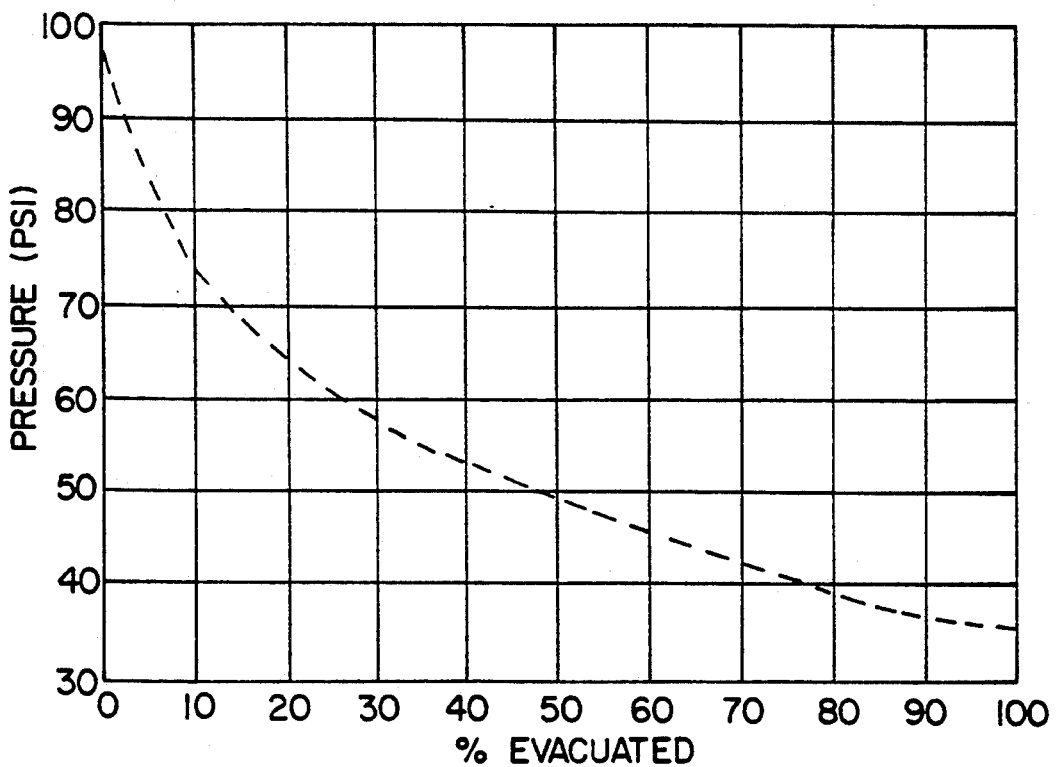
FIG. 3 is a graph of pressure versus depth of discharge for a dispenser employing a carbon dioxide propellant, acetone and a different preferred macroporous polymeric matrix according to the present invention.

As a further example, a polymeric material as produced in Example 9 was tested in the same vapor-tight container. The polymers employed in this test had a porosity of greater than 3.0 cc/gram. 1.11 g polymer, 8.4 ml acetone and 1.11 g carbon dioxide were added to the container and the resulting discharge curve is shown in FIG. 3. The end pressure taken 5 minutes after extrusion was complete was 39 psi.

Figure 4:
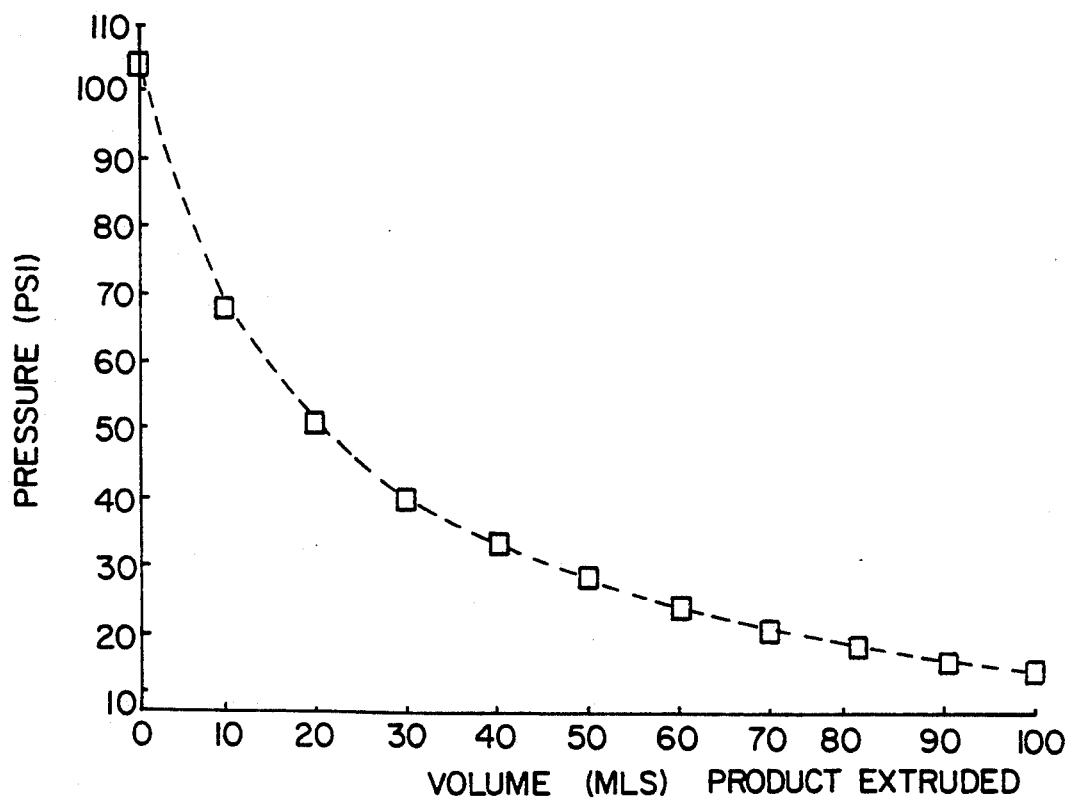
FIG. 4 is a graph of pressure versus depth of discharge for dispenser pressurized with carbon dioxide propellant only.

FIG. 4 shows the discharge curve for a pressurized, vapor-tight bag-type container charged with carbon dioxide only. No macroporous polymer was employed. As shown, the pressure is initially near 105 psi and drops off gradually as the container is evacuated until a final pressure of less than 20 psi is reached.

While certain modifications and variations have been described above the invention is not restricted thereto, and other modifications and variations can be adopted without departing from the scope of the invention as defined in the appended claims.

What is claimed is:

1. A process for preparing a pellet for use in pressurized dispensing containers, said method comprising the following steps:
   mixing substantially rigid crosslinked polymer macroporous particles with a binder to form a mixture of polymer macroporous particles and binder; and
   compressing the mixture of polymer macroporous particles to form a pellet, wherein said polymer macroporous particles define a substantially non-collapsible pore network and said pellet defines interstitial spaces between said polymer macroporous particles, and wherein the interstitial spaces are substantially larger than the pore network.

2. A process as recited in claim 1 wherein the particles have a particle size of between about 1 and about 500 $\mu$m; a particle density of between about 0.1 and about 2.0 g/cc; a pore volume of between about 0.5 and about 6.0 cc/g; an average pore diameter of between about 0.001 and about 3 $\mu$m; and a surface area of between about 1 and about 500 $m^2/g$.

3. A process as recited in claim 1 wherein the binder is selected from a group consisting of hydrogenated cottonseed oil, polyvinyl alcohol, polyvinylpyrrolidone, and microcrystalline cellulose.

4. A process as recited in claim 1 wherein said particles are composed of a copolymer of methacrylate and ethylene glycol dimethylmethacrylate.

5. A process as recited in claim 1 wherein the particles range from about 10 mesh to about 21 mesh.

6. A process as recited in claim 1 wherein said polymer particles are texturized by a pretreatment, said pretreatment comprising the following steps:
   washing the particles with hot water, and
   washing the particles with acetone.

7. A process as recited in claim 1 wherein monomers are polymerized in an organic porogen suspended in an aqueous phase to form said polymeric particles, wherein said polymer particles are pretreated by heating to remove substantially all of said porogen.

* * * * *